United States Patent
Gliner

(10) Patent No.: US 10,685,486 B2
(45) Date of Patent: Jun. 16, 2020

(54) LOCATING AN OPENING OF A BODY CAVITY

(71) Applicant: Biosense Webster (Israel) Ltd., Yokneam (IL)

(72) Inventor: Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 196 days.

(21) Appl. No.: 15/940,613

(22) Filed: Mar. 29, 2018

(65) Prior Publication Data

US 2019/0304187 A1    Oct. 3, 2019

(51) Int. Cl.
| | |
|---|---|
| G06T 19/00 | (2011.01) |
| A61B 6/03 | (2006.01) |
| G06T 7/00 | (2017.01) |
| A61B 1/31 | (2006.01) |
| A61B 6/00 | (2006.01) |

(52) U.S. Cl.
CPC ............ *G06T 19/003* (2013.01); *A61B 6/032* (2013.01); *G06T 7/0012* (2013.01); *A61B 1/31* (2013.01); *A61B 6/466* (2013.01); *G06T 2207/10081* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 7,623,900 | B2 * | 11/2009 | Graham | G06T 19/003 382/128 |
| 7,853,058 | B2 * | 12/2010 | Gauldie | A61B 6/032 345/419 |
| 2003/0152897 | A1 * | 8/2003 | Geiger | G06T 15/00 434/262 |
| 2007/0052724 | A1 * | 3/2007 | Graham | G06T 19/003 345/620 |
| 2008/0118117 | A1 * | 5/2008 | Gauldie | A61B 6/032 382/128 |
| 2008/0161730 | A1 * | 7/2008 | McMahon | A61B 5/1076 600/593 |

(Continued)

OTHER PUBLICATIONS

European Search Report dated Jun. 18, 2019 from corresponding European Patent Application No. 19165877.2.

(Continued)

*Primary Examiner* — Anand P Bhatnagar
(74) *Attorney, Agent, or Firm* — Todd J. Burns

(57) ABSTRACT

Methods, apparatus and computer program products implement embodiments of the present invention that include receiving three-dimensional (3D) image data with respect to a 3D region including body tissue in a living body, and segmenting the 3D image data so as to identify a cavity within the body tissue and a wall surrounding the cavity. For each point among a plurality of points in the cavity, a respective minimum distance from the point to the wall is found, and among the plurality of the points, a set of one or more points for which the respective minimum distance is a local maximum relative to neighboring points in the plurality is found. One of the points in the set for which the respective minimum distance is minimal among the one or more points in the set is then identified as an entrance to the cavity.

21 Claims, 7 Drawing Sheets

(56) References Cited

U.S. PATENT DOCUMENTS

| | | | |
|---|---|---|---|
| 2015/0087981 A1* | 3/2015 | Ishii | G06T 19/003 |
| | | | 600/440 |
| 2015/0213629 A1* | 7/2015 | Celi | A61B 5/0066 |
| | | | 382/128 |
| 2016/0279388 A1* | 9/2016 | Barrish | A61M 25/0155 |
| 2017/0021143 A1* | 1/2017 | Barrish | A61M 25/0155 |
| 2017/0157363 A1* | 6/2017 | Barrish | A61M 25/0074 |
| 2018/0368666 A1* | 12/2018 | Yeung | A61B 1/015 |
| 2019/0340838 A1* | 11/2019 | Gluhovsky | A61B 5/068 |

OTHER PUBLICATIONS

Bister, M et al., "Towards Automated Analysis in 3D Cardiac MR Imaging"; Jul. 7, 1991, Information Processing in Medical Imaging, Springer Berlin Heidelberg, Berlin, Heidelberg, pp. 205-217.

Frimmel, Hans et al, "Fast and Robust Computation of Colon Centerline in CT Colonography", Medical Physics, AIP, Melville, NY, US, vol. 31, No. 11, Oct. 27, 2004, pp. 3046-3056.

\* cited by examiner

LOCATING AN OPENING OF A BODY CAVITY

CROSS-REFERENCE TO RELATED APPLICATIONS

This application is related to U.S. patent application titled "Static Virtual Camera Positioning" filed on even date with the present application, which is incorporated herein by reference.

FIELD OF THE INVENTION

The present invention relates generally to image presentation, and specifically to locating an opening of a body cavity that can be used for positioning of a static virtual camera that presents a three-dimensional image from a selected vantage point within the image.

BACKGROUND OF THE INVENTION

Some medical procedures are performed using a three-dimensional (3D) image of a patient. One example of a 3D image used in medical procedures is a computed tomography (CT) scan which combines multiple X-ray measurements taken from different angles to produce cross-sectional virtual "slices" of specific areas of a patient, thereby enabling a physician to see inside the patient without a need for surgery.

U.S. Patent Application 2003/0152897 to Geiger describes a method for automatic navigation during a virtual endoscopy, by navigating a viewpoint of a virtual endoscope in a lumen of a structure. The method includes determining an initial viewpoint of the virtual endoscope, and determining a longest ray from the initial viewpoint to the lumen.

U.S. Patent Application 2008/0118117 to Gauldie et al., describes a method for orienting a virtual camera for rendering a virtual endoscopy image of a lumen in a biological structure. The method includes calculating suitable paths that avoid a wall in the lumen by using ray casting to find the longest ray from a camera position to the wall.

U.S. Patent Application 2007/0052724 to Graham et al., describes a method for navigating along a biological object with a lumen represented by a three-dimensional volume data set. The method includes generating a multiple navigation segments connectable in a sequence, casting groups of rays outwards from the start point of the segment to the object wall to determine respective directions of each segment, and calculating an average ray length for each of the groups.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention a method for medical imaging, including receiving, by a processor, three-dimensional (3D) image data with respect to a 3D region including body tissue in a living body, segmenting the 3D image data so as to identify a cavity within the body tissue and a wall surrounding the cavity, for each point among a plurality of points in the cavity, finding a respective minimum distance from the point to the wall, finding, among the plurality of the points, a set of one or more points for which the respective minimum distance is a local maximum relative to neighboring points in the plurality, and identifying as an entrance to the cavity one of the points in the set for which the respective minimum distance is minimal among the one or more points in the set.

In some embodiments, the method includes using the identified point as a seed location for positioning a virtual camera within the cavity. In another embodiment, prior to finding the minimum distance for each point, the method includes filling the body cavity with the points.

In additional embodiments, filling the body cavity with the points includes selecting an origin location in the cavity and a radius, and applying a fill algorithm to fill, an area in the body cavity included in a spherical region including the origin and the radius, with the points. In further embodiments, the fill algorithm includes a flood-fill algorithm.

In one embodiment, the 3D image data includes a computed tomography scan. In supplemental embodiments, the cavity includes a sinus passageway and a sinus cavity, and wherein the opening includes the opening from the sinus passageway to the sinus cavity.

In some embodiments, the points include spheres having an initial diameter and respective coordinates, wherein finding the local minimum distance for each given point includes growing the diameter of the given sphere until the coordinates of the given sphere intersect coordinates of the wall, wherein finding the set of one or more points for which the respective minimum distance is the local maximum relative to neighboring points in the plurality includes finding a sphere set of one or more spheres for which the respective grown diameters are a local maximum relative to the respective grown diameters of neighboring grown spheres in the plurality, and wherein identifying one of the points includes identifying one of the spheres in the sphere set for which the respective grown diameter is minimal among the one or more spheres in the sphere set. In additional embodiments the neighboring grown spheres include nearest-neighboring grown spheres to the given sphere.

In further embodiments, the points include spheres having an initial, wherein finding the local minimum distance for each given point includes growing the diameter and moving each given sphere until it gets stuck in the cavity, and wherein identifying one of the points includes identifying one of the spheres in the sphere set having the shortest grown diameter.

There is also provided, in accordance with an embodiment of the present invention an apparatus for medical imaging, including a an input/output (I/O) communications interface, and a processor configured to receive, via the I/O interface, three-dimensional (3D) image data with respect to a 3D region including body tissue in a living body, to segment the 3D image data so as to identify a cavity within the body tissue and a wall surrounding the cavity, for each point among a plurality of points in the cavity, to find a respective minimum distance from the point to the wall, to find, among the plurality of the points, a set of one or more points for which the respective minimum distance is a local maximum relative to neighboring points in the plurality, and to identify as an entrance to the cavity one of the points in the set for which the respective minimum distance is minimal among the one or more points in the set.

There is further provided, in accordance with an embodiment of the present invention, computer software product, the product including a non-transitory computer-readable medium, in which program instructions are stored, which instructions, when read by a computer, cause the computer to receive three-dimensional (3D) image data with respect to a 3D region including body tissue in a living body, to segment the 3D image data so as to identify a cavity within the body tissue and a wall surrounding the cavity, for each point among a plurality of points in the cavity, to find a respective minimum distance from the point to the wall, to find, among the plurality of the points, a set of one or more points for which the respective minimum distance is a local maximum relative to neighboring points in the plurality, and to identify as an entrance to the cavity one of the points in the set for which the respective minimum distance is minimal among the one or more points in the set.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Three-dimensional (3D) images, such as computed tomography (CT) images, can be used help physician view one or more body cavities in a patient before or during a medical procedure. The 3D images enable the body cavities to be viewed from different vantage points. These vantage points may also be referred to as "virtual cameras" that can be placed at different locations in the patient.

Some otorhinolaryngological (ENT) procedures involve navigation of a guidewire through a narrow sinus opening. Before or during these procedures, it may be difficult for a physician to accurately place a virtual camera at a position that can observe the narrow opening (i.e., in order to provide a visual guide to the physician while maneuvering the guidewire into the opening). Reasons for this difficulty include:

The sinus openings are typically small and/or narrow.

The CT images that are used are two-dimensional (2D) slices/projections, whereas the virtual camera needs to be placed in a 3D coordinate system.

The physician typically has very little time to try to adjust the position and orientation of the camera.

Embodiments of the present invention provide methods and systems for medical imaging that can detect an opening of a body cavity such as a sinus opening. As described hereinbelow, three-dimensional (3D) image data with respect to a 3D region is received, the 3D region comprising body tissue in a living body. The 3D image data is segmented so as to identify a cavity within the body tissue and a wall surrounding the cavity, and for each point among a plurality of points in the cavity, a respective minimum distance from the point to the wall is found. Among the plurality of the points, a set of one or more points for which the respective minimum distance is a local maximum relative to neighboring points in the plurality is found, and one of the points in the set for which the respective minimum distance is minimal among the one or more points in the set is identified as an entrance to the cavity.

In some embodiments, the point identified as the entrance to the cavity can be used as a seed location when identifying a location for a virtual camera in the cavity.

System Description

Figure 1:
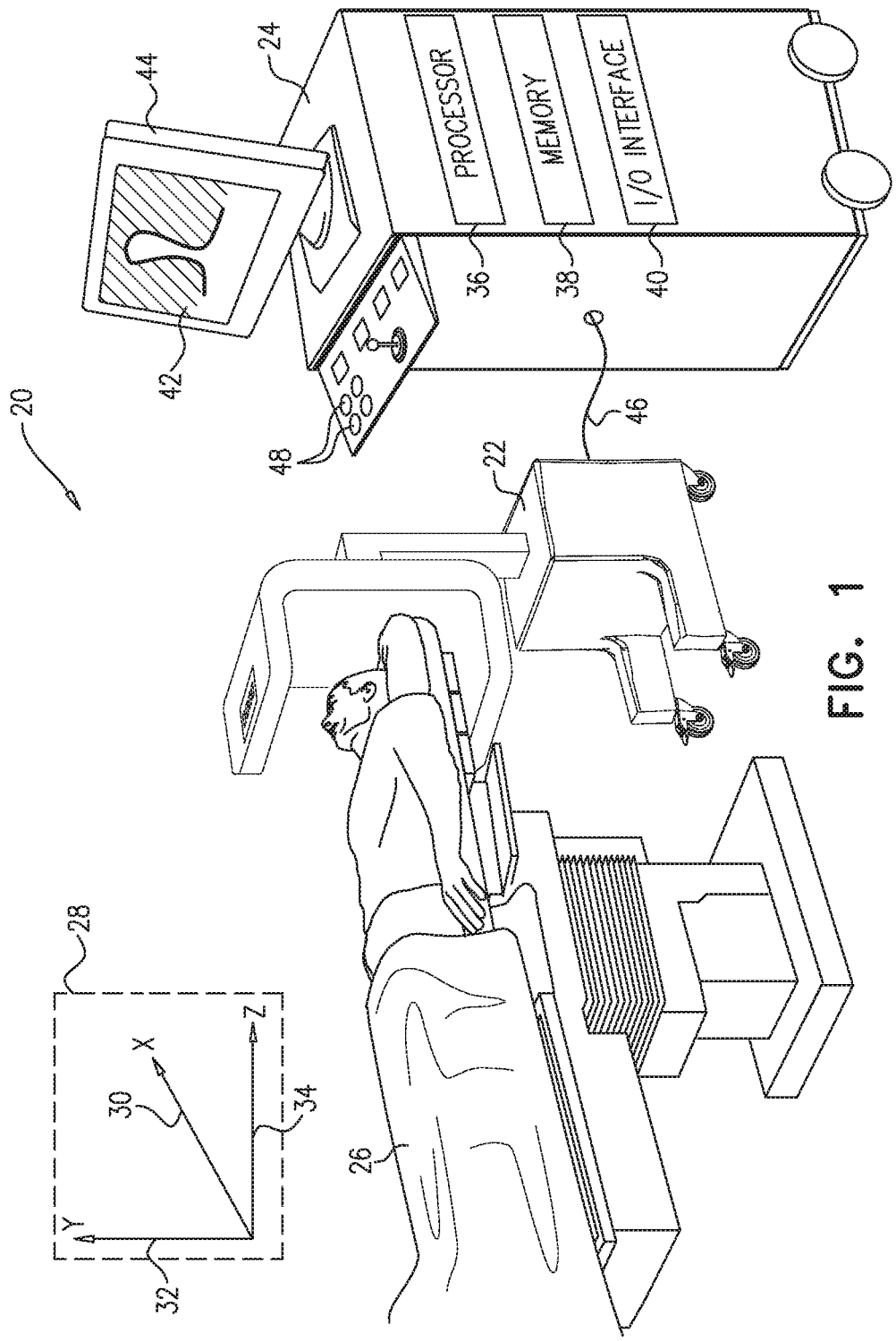
FIG. 1 is a schematic pictorial illustrations of a three-dimensional (3D) medical imaging system configured to locate an opening of a body cavity in a patient, in accordance with an embodiment of the present invention.

FIG. 1 shows a schematic pictorial illustration of a medical imaging system 20 configured to locate an opening of a body cavity in a patient, in accordance with an embodiment of the present invention. Medical imaging system 20 comprises a computed tomography (CT) scanner 22 and a control console 24. In embodiments described herein, it is assumed that medical imaging system 20 is used for diagnostic or therapeutic treatment.

Prior to performing an invasive medical procedure on a patient 26, computed tomography scanner 22 generates electrical signals comprising image data for a lumen (e.g., a nasal cavity or a paranasal sinus) of the patient, and conveys the generated image data to control console 24. Computed tomography scanner generates the image data in an image coordinate system 28 comprising an X-axis 30, a Y-axis 32 and a Z-axis 34. The X, Y and Z axes are typically parallel to intersections of the median, coronal, and axial planes of patient 26.

Control console 24 comprises a processor 36, a memory 38 and an input/output (I/O) communications interface 40. In operation, processor 36 uses the received image data to present an image 42 (also referred to herein as image slice 42) on a display screen 44. Memory 38 stores the image data, and I/O communications interface 40 enables the control console to transfer signals from, and/or transfer signals to CT scanner 22 via a wired connection 46.

Display 44 is assumed, by way of example, to comprise a flat panel display such as a liquid crystal display, a light emitting diode display, an organic light-emitting diode display or a plasma display. However, other display devices can also be employed to implement embodiments of the present invention. In some embodiments, display 44 may comprise a touchscreen that, in addition to presenting image 42, can be configured to accept inputs from an operator (not shown).

In some embodiments, the operator (also referred to herein as a medical professional) can manipulate the image data, typically by presenting images in slices orthogonal to the X, Y, or Z axes on display 44, using one or more input devices 48. In embodiments where display 44 comprises a touchscreen display, the operator can manipulate the image data and a given image slice via the touchscreen display.

Processor 36 typically comprises a general-purpose computer, with suitable front end and additional interface circuits for receiving signals from CT scanner 22 and controlling the other components of control console 24. Processor 36 may be programmed in software to carry out the functions that are described herein. The software may be downloaded to control console 24 in electronic form, over a network, for example, or it may be provided on non-transitory tangible media, such as optical, magnetic or electronic memory media. Alternatively, some or all of the functions of processor may be carried out by dedicated or programmable digital hardware components.

Body Cavity Opening Detection

Figure 2:
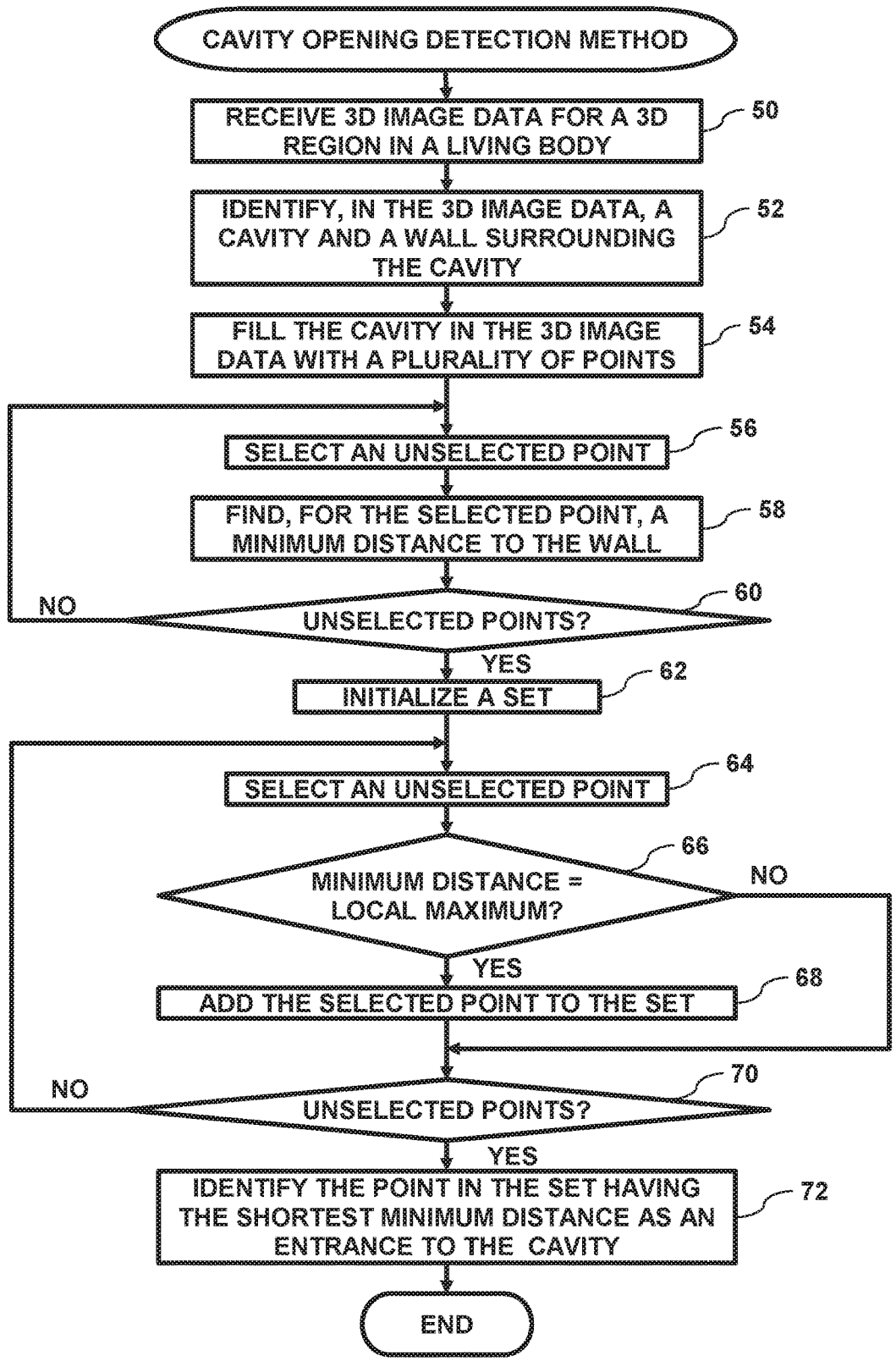
FIG. 2 is a flow diagram that schematically illustrates a method of locating the opening of the body cavity, in accordance with an embodiment of the present invention.
Figure 3:
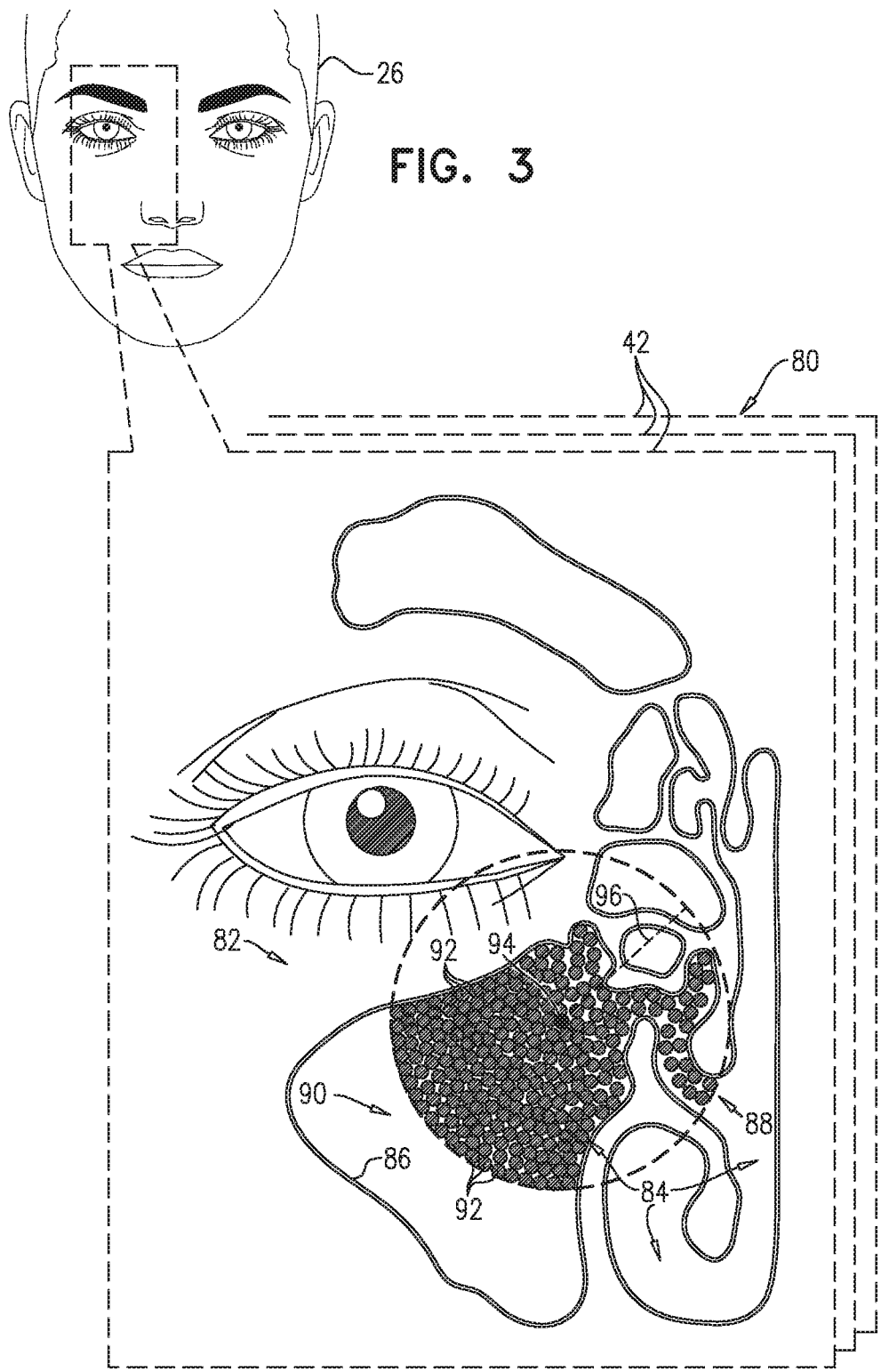
FIG. 3 is a schematic pictorial illustration showing a two-dimensional image of the body cavity filled with points, in accordance with an embodiment of the present invention.
Figure 4:
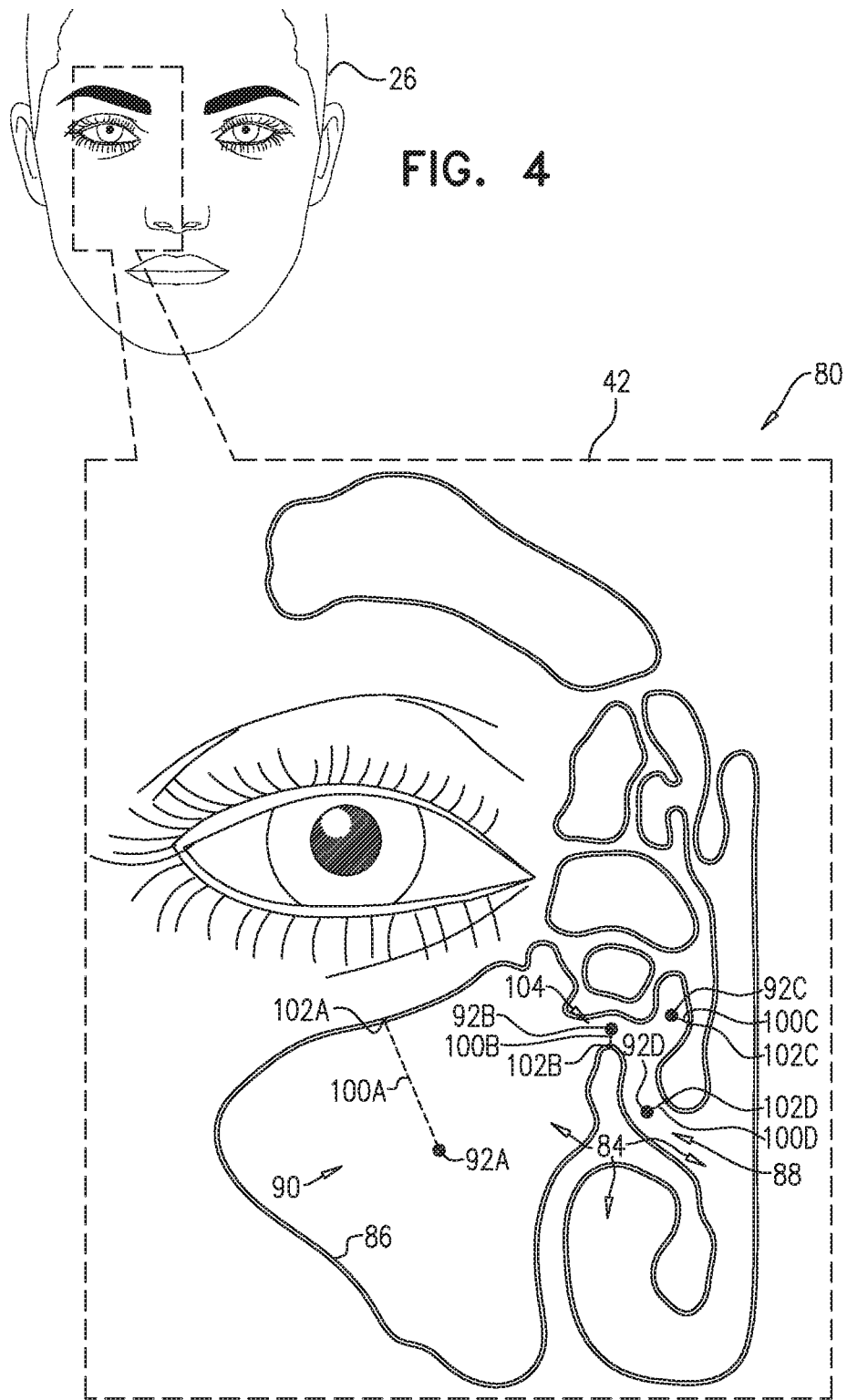
FIG. 4 is a schematic pictorial illustration showing a two-dimensional image of a set of the points whose respective minimum distances to a wall of the body cavity are local maximums relative to their respective neighboring points, in accordance with an embodiment of the present invention.

FIG. 2 is a flow diagram that schematically illustrates a method of detecting an opening in a body cavity of patient 26, and FIGS. 3 and 4 are a schematic pictorial illustrations of a given image slice 42 of a 3D region 80 in patient 26, in accordance with an embodiment of the present invention. In a receive step 50, processor 36 receives, from CT scanner, 3D image data for 3D region 80 comprising body tissue 82, and in a first identification step 52, the processor segments the 3D image data so as to identify a cavity 84 within body tissue 82 and a wall 86 surrounding the cavity. In the example shown in FIG. 3, cavity 84 comprises a sinus passageway 88 that opens to a sinus cavity 90.

In a fill step 54, processor 36 fills cavity 84 (i.e., in given image slice 42) with a plurality of points 92 (FIG. 3) having respective coordinates in coordinate system 28. In one embodiment, processor 36 can fill cavity 74 with points 92 by selecting initial coordinates for an origin 94, specifying a radius 96, and using a fill algorithm such as a flood fill algorithm to fill a 3D portion of body cavity (i.e., the region within the radius emanating from the origin) with points 92. As described hereinbelow in the description referencing FIGS. 5-7, points 92 may also be referred to herein as spheres 92.

In a first selection step 56, processor 36 selects an unselected point 92, and in a find step 58, the processor finds, for the selected point, a minimum distance 100 from the selected point to wall 86 (FIG. 4). In other words, processor 36 finds a location 102 (also referred to herein as wall location 102) on wall 86 that is closest to the selected point, and identifies minimum distance 100 between the selected point and the found location as the minimum distance for the selected point. In the example shown in FIG. 4, only four selected minimum distances 100A-100D are shown for four selected points 92A-92D for purposes of visual simplicity. The selection of points such as 92A-92D and minimum distances such as 100-100D is described below.

In a first comparison step 60, if there are additional unselected points 92, then processor 36 returns to step 56. When processor 36 has found all minimum distances 100 for all points 92 (i.e., all the points have been selected), then in an initialization step 62, the processor initializes a set of local maxima (i.e., of the minimum distances). In a second selection step 64, upon initializing the set of local maxima, processor 36 initiates a new selection process by selecting a given point 92.

In a second comparison step 66, processor 36 compares the minimum distance for the selected point to the minimum distances of neighboring points 92 (i.e., the points surrounding the selected point), and if the minimum distance for the selected point is a local maximum relative to the minimum distances of the neighboring points, then the processor adds the selected point to the set in an addition step 68.

In a third comparison step 70, if there any unselected points 92, then the method continues with step 64. Returning to step 66, if the minimum distance for the selected point is not a local maximum relative to the minimum distances of the neighboring points, then the method continues with step 70. Returning to step 70, if there are no unselected points 92, then in a second identification step 72, processor 36 identifies, in the set, a given point 92 having the shortest, i.e., smallest, minimum distance as an entrance 104 to cavity 84, and the method ends.

In the example shown in FIG. 4, points 92A-92D comprise the points whose respective minimum distances 100 are local maximums relative to the minimum distances of their respective neighboring points 92. The minimum distances and the wall locations corresponding to points 92A-92D can be differentiated by appending a letter to the identifying numeral, so that the minimum distances comprises minimum distances 100A-100D, and the wall locations comprise wall locations 102A-102D.

In the example shown in FIG. 4, processor 36 identifies point 92B as having the shortest minimum distance. Therefore, in the example shown in FIG. 4, entrance 104 comprises the coordinates of point 92B.

In some embodiments, entrance 104 comprises an entrance from sinus passageway 88 to sinus cavity 90 (or vice versa), and the entrance can be used as a seed location when identifying a camera location for a virtual camera in the cavity.

Figure 5:
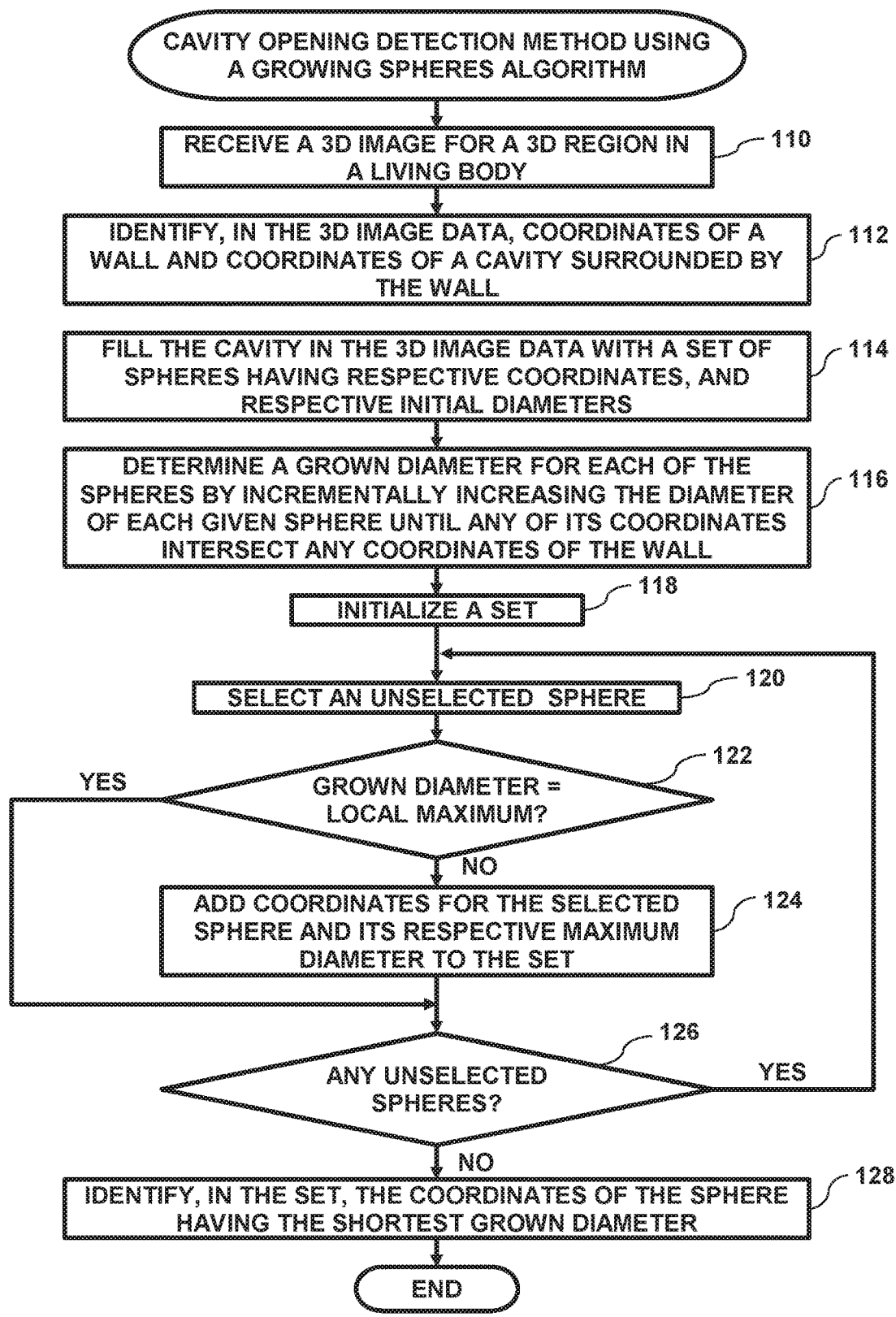
FIG. 5 is a flow diagram that schematically illustrates a method of using a growing spheres algorithm to locate the opening of the body cavity, in accordance with a first alternative embodiment of the present invention.
Figure 6:
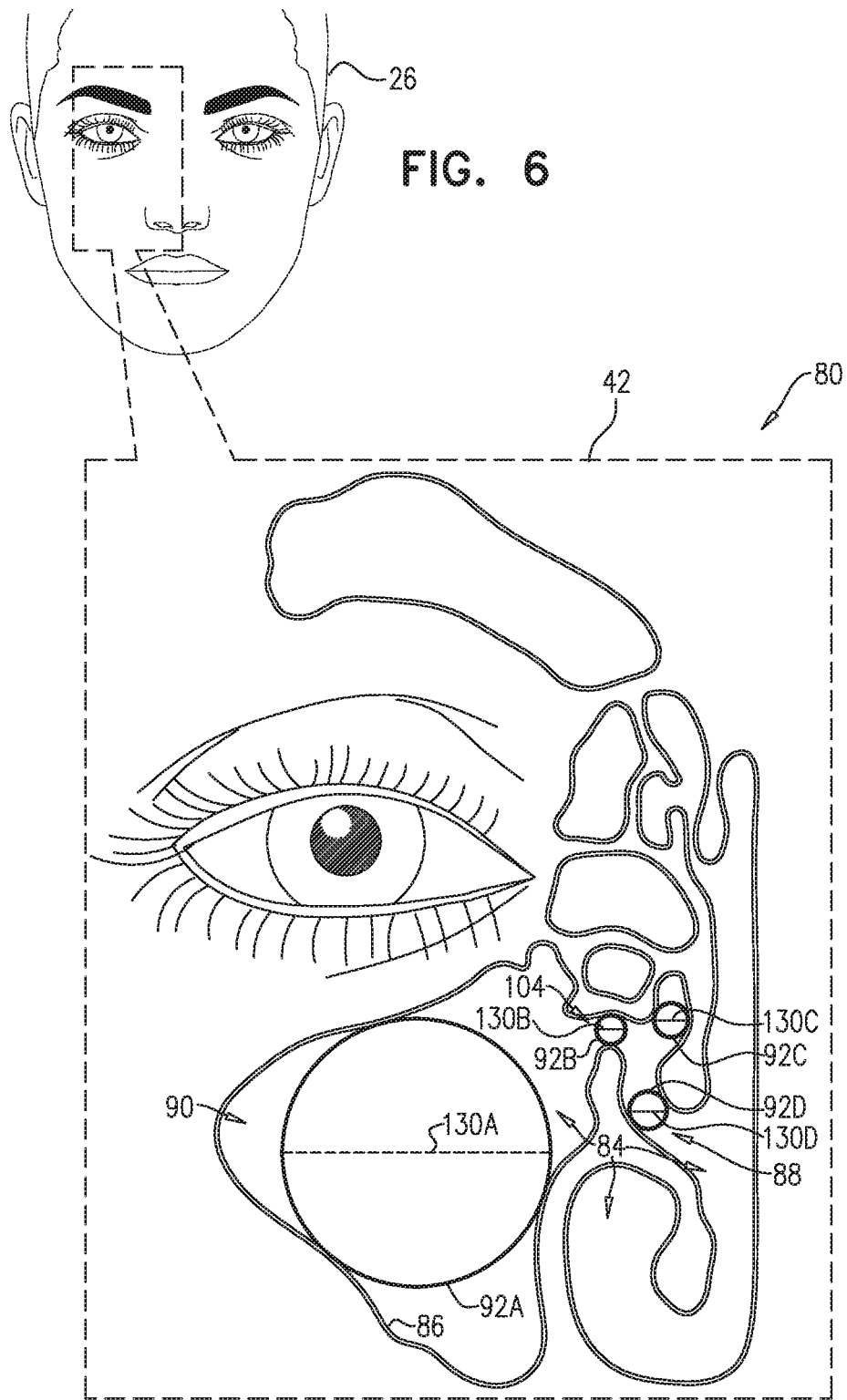
FIG. 6 is a schematic pictorial illustration showing the body cavity comprising grown spheres used by the growing spheres algorithm, in accordance with an embodiment of the present invention.

FIG. 5 is a flow diagram that schematically illustrates a method of using a growing spheres algorithm to find entrance 104, and FIG. 6 is a schematic pictorial illustration of a given image slice 42 of 3D region 80 in patient 26, in accordance with a first alternative embodiment of the present invention. In FIG. 5, a receive step 110 and an identification step 112 are substantially the same as steps 50 and 52 in FIG. 2, as described supra.

In a fill step 114, processor 36 fills, in the 3D image data, cavity 84 with a plurality of spheres 92. As described supra, points 92 may also be referred to herein as spheres 92. As shown in FIG. 6, each sphere 92 has a respective diameter 130 and respective coordinates in coordinate system 28. When processor fills cavity 84 with the plurality of spheres, each of the spheres has a small initial diameter 130 (e.g., 0.5 mm).

In a growing step 116, processor 36 determines a "grown" diameter 130 for each sphere 92 by incrementally increasing the diameter of each of given sphere 92 until any coordinates of the grown sphere intersects any of the coordinates of wall 86. In some embodiments, processor can incrementally increase the diameter of each given sphere by a fixed amount (e.g., the initial diameter).

In an initialization step 118, processor 36 initializes a set of local maxima (i.e., of the minimum distances, as described supra), and in a selection step 120, the processor selects an unselected grown sphere 92. In a first comparison step 122, if the grown diameter of the grown sphere of the selected sphere is a local maximum relative to the grown diameters of the neighboring spheres (in other words, the grown diameter of the selected sphere is greater than or equal to all the grown diameters of the spheres that immediately surround the selected sphere), then, in an addition step 124, processor 36 adds the selected sphere, including its coordinates and its grown diameter, to the set. In some embodiments, the neighboring spheres comprise nearest-neighboring spheres to the selected sphere, so that the grown diameter of the selected sphere is greater than or equal to all the grown diameters of the spheres that immediately surround the selected sphere.

In a second comparison step 126, if there are any remaining unselected spheres then the method continues with step 120. Returning to step 122, if the grown diameter of the grown sphere of the selected sphere is not a local maximum relative to the grown diameters of the neighboring spheres, then the method continues with step 126.

Returning to step 126, if there are no unselected spheres, then in a second identification step 128, processor 36 identifies, in the set the coordinates of the sphere having the shortest, i.e., smallest, grown diameter, and the method ends. In the example shown in FIG. 5, the identified sphere comprises sphere 92B (which corresponds to point 92B in FIG. 4)

As described in the description referencing FIG. 2 hereinabove, embodiments of the present invention identify entrance 104 by (a) finding, for each point 92 among a plurality of the points in cavity 84, the respective minimum distance 100 from the point to wall 86, (b) finding, among the plurality of the points, a set of one or more the points for which the respective minimum distance is a local maximum relative to neighboring points 92 in the plurality (steps 64-70 in FIG. 2), and (c) identifying as the entrance to the cavity one of the points in the set for which the respective minimum distance is minimal among the one or more points in the set (step 72 in FIG. 2).

In the embodiment presented in FIG. 5 and FIG. 6, step 116 in FIG. 5 corresponds to steps 56-60 in FIG. 2, steps 120-126 in FIG. 5 correspond to steps 64-70 in FIG. 2, and step 128 in FIG. 5 corresponds to step 72 in FIG. 2. In other words, in the embodiment described in FIG. 5, processor 36 can (a) find the respective minimum distances by performing step 116, (b) find the set of the one or more points (i.e., the local maxima) by performing steps 120-126, and (c) identify the entrance by performing step 128.

In this first alternative embodiment of the present invention), the coordinates identified in step 128 indicate an opening from sinus passageway 88 into sinus cavity 90. There may be instances where the set comprises multiple spheres 92 having identical grown diameters. Since these spheres (i.e., having identical shortest grown diameters) will typically be adjacent to one another, processor 36 can select the coordinates of one of these spheres as the entrance to sinus cavity 90. For example, of the spheres having the same grown diameter, processor 36 can select the coordinates of the sphere closest to origin 94. Alternatively, processor 36 can present the spheres on display 44 by overlaying the spheres on the image slice, and a user (not shown) can use input devices 48 to select one of the presented spheres.

Figure 7:
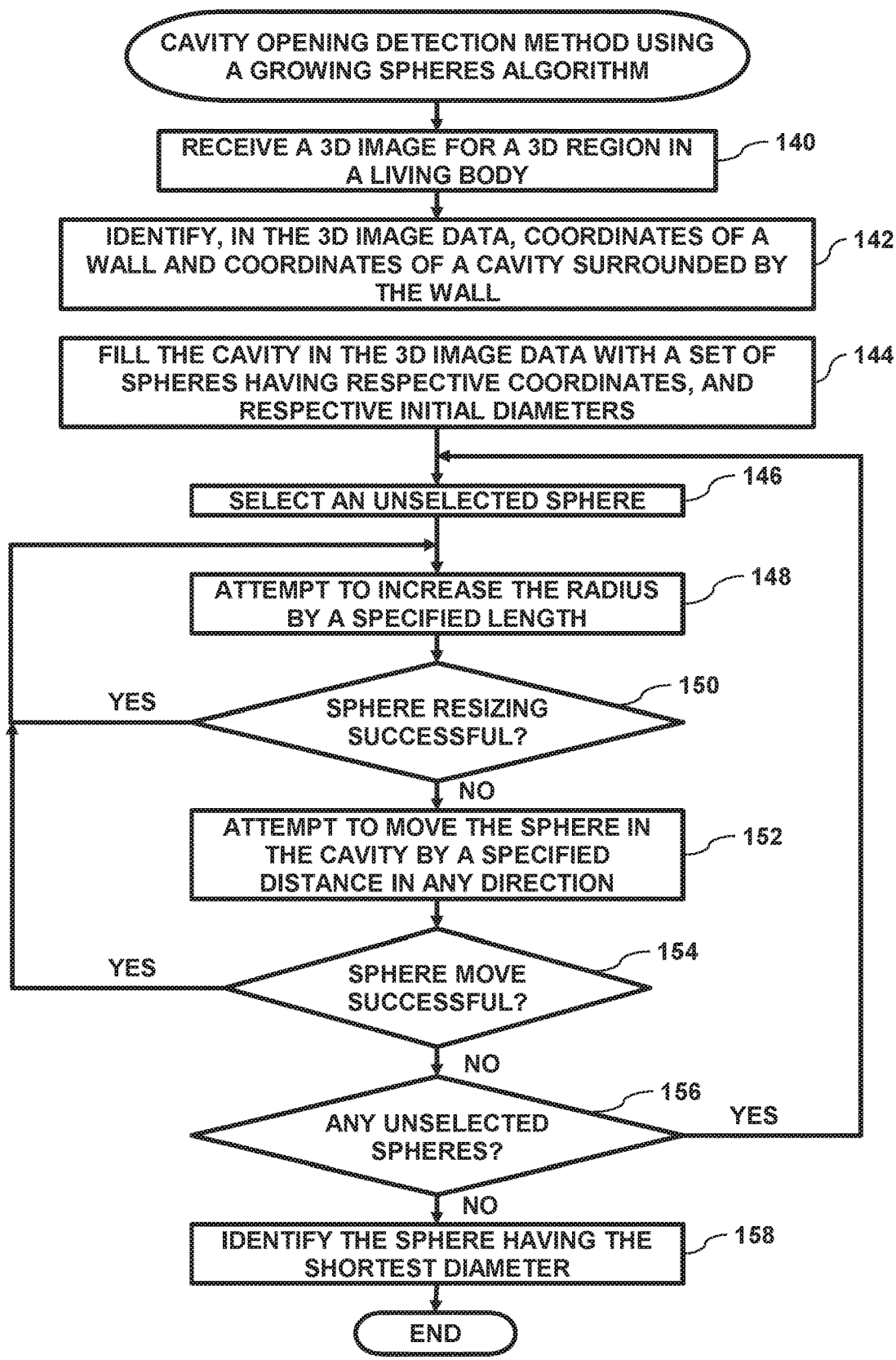
FIG. 7 is a flow diagram that schematically illustrates a method of using the growing spheres algorithm to locate the opening of the body cavity, in accordance with a second alternative embodiment of the present invention.

FIG. 7 is a flow diagram that schematically illustrates a method of using the growing spheres algorithm to find entrance 104, in accordance with a second alternative embodiment of the present invention. In FIG. 7, a receive step 140 and a first identification step 142 are substantially the same as steps 50 and 52 in FIG. 2 (and steps 110 and 112 in FIG. 5), as described supra. Additionally, a fill step 144 is substantially the same as step 114 in FIG. 5, as described hereinabove.

In a selection step 146, processor 36 selects an unselected sphere 92, and in a grow step 148, the processor attempts to grow the selected sphere by increasing the diameter of the selected sphere by a specified length (e.g., the initial diameter 130 of the selected sphere). In embodiments of the present invention, step 148 is successful if none of the coordinates of the grown sphere matches any of the coordinates of wall 86.

In a first comparison step 150, if the attempt to grow the selected sphere in step 148 was successful, then the method continues with step 148. However, if the attempt to grow the selected sphere in step 148 was not successful, then in a move step 152, processor 36 attempts to move the selected sphere by a specified distance (e.g., the initial diameter 130 of the selected sphere) in any direction. In embodiments of the present invention, step 152 is successful if none of the coordinates of the moved sphere matches any of the coordinates of wall 86.

In a second comparison step 154, if the attempt to move the sphere in step 152 was successful then the method continues with step 148. However, if the attempt to move the sphere in step 142 was not successful, then the selected sphere is "stuck" (i.e., the selected sphere cannot be grown or moved), and in a third comparison step 156, processor 36 checks if there are any remaining unselected spheres 92. If there are any unselected spheres 92, then the method continues with step 146. If there are no remaining unselected spheres 92, then in a second identification step 158, processor 36 identifies the initial coordinates of the grown sphere having the shortest, i.e., smallest, diameter as the coordinates for entrance 104, and the method ends.

As described supra, embodiments of the present invention identify entrance 104 by first finding, for each point 92 among a plurality of the points in cavity 84, the respective minimum distance 100 from the point to wall 86 (steps 56-60 in FIG. 2), finding, among the plurality of the points, a set of one or more the points for which the respective minimum distance is a local maximum relative to neighboring points 92 in the plurality (steps 64-70 in FIG. 2), and identifying as the entrance to the cavity one of the points in the set for which the respective minimum distance is minimal among the one or more points in the set (step 72 in FIG. 2). In the embodiment present in FIG. 7, processor 36 can find the respective minimum distances (i.e., steps 56-60) and can find the set of the one or more points (i.e., steps 64-70) by performing steps 146-156, and the processor can identify the entrance (i.e., step 72) by performing step 158.

As described in the description referencing FIG. 5 hereinabove, there may be instances where the set comprises multiple spheres 92 having identical grown diameters. In these instances, processor 36 can identify the coordinates for entrance 104 using the embodiments described supra.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for medical imaging, comprising:
   receiving, by a processor, three-dimensional (3D) image data with respect to a 3D region comprising body tissue in a living body;
   segmenting the 3D image data so as to identify a cavity within the body tissue and a wall surrounding the cavity;
   for each point among a plurality of points in the cavity, finding a respective minimum distance from the point to the wall;
   finding, among the plurality of the points, a set of one or more points for which the respective minimum distance is a local maximum relative to neighboring points in the plurality; and
   identifying as an entrance to the cavity one of the points in the set for which the respective minimum distance is minimal among the one or more points in the set.

2. The method according to claim 1, and comprising using the identified point as a seed location for positioning a virtual camera within the cavity.

3. The method according to claim 1, and comprising prior to finding the minimum distance for each point, filling the body cavity with the points.

4. The method according to claim 3, wherein filling the body cavity with the points comprises selecting an origin location in the cavity and a radius, and applying a fill algorithm to fill, an area in the body cavity included in a spherical region comprising the origin and the radius, with the points.

5. The method according to claim 4, wherein the fill algorithm comprises a flood-fill algorithm.

6. The method according to claim 1, wherein the 3D image data comprises a computed tomography scan.

7. The method according to claim 1, wherein the cavity comprises a sinus passageway and a sinus cavity, and wherein the opening comprises the opening from the sinus passageway to the sinus cavity.

8. The method according to claim 1, wherein the points comprise spheres having an initial diameter and respective coordinates, wherein finding the local minimum distance for each given point comprises growing the diameter of the given sphere until the coordinates of the given sphere intersect coordinates of the wall, wherein finding the set of one or more points for which the respective minimum distance is the local maximum relative to neighboring points in the plurality comprises finding a sphere set of one or more spheres for which the respective grown diameters are a local maximum relative to the respective grown diameters of neighboring grown spheres in the plurality, and wherein identifying one of the points comprises identifying one of the spheres in the sphere set for which the respective grown diameter is minimal among the one or more spheres in the sphere set.

9. The method according to claim 8, wherein the neighboring grown spheres comprise nearest-neighboring grown spheres to the given sphere.

10. The method according to claim 1, wherein the points comprise spheres having an initial, wherein finding the local minimum distance for each given point comprises growing the diameter and moving each given sphere until it gets stuck in the cavity, and wherein identifying one of the points comprises identifying one of the spheres in the sphere set having the shortest grown diameter.

11. An apparatus for medical imaging, comprising:
    an input/output (I/O) communications interface; and
    a processor configured:
       to receive, via the I/O interface, three-dimensional (3D) image data with respect to a 3D region comprising body tissue in a living body,
       to segment the 3D image data so as to identify a cavity within the body tissue and a wall surrounding the cavity,
       for each point among a plurality of points in the cavity, to find a respective minimum distance from the point to the wall,
       to find, among the plurality of the points, a set of one or more points for which the respective minimum distance is a local maximum relative to neighboring points in the plurality, and
       to identify as an entrance to the cavity one of the points in the set for which the respective minimum distance is minimal among the one or more points in the set.

12. The apparatus according to claim 11, wherein the processor is configured to use the identified point as a seed location for positioning a virtual camera within the cavity.

13. The apparatus according to claim 11, wherein prior to finding the minimum distance for each point, the processor is configured to fill the body cavity with the points.

14. The apparatus according to claim 13, wherein the processor is configured to fill the body cavity with the points by selecting an origin location in the cavity and a radius, and applying a fill algorithm to fill, an area in the body cavity included in a spherical region comprising the origin and the radius, with the points.

15. The apparatus according to claim 14, wherein the fill algorithm comprises a flood-fill algorithm.

16. The apparatus according to claim 11, wherein the 3D image data comprises a computed tomography scan.

17. The apparatus according to claim 11, wherein the cavity comprises a sinus passageway and a sinus cavity, and wherein the opening comprises the opening from the sinus passageway to the sinus cavity.

18. The apparatus according to claim 11, wherein the points comprise spheres having an initial diameter and respective coordinates, wherein the processor is configured to find the local minimum distance for each given point by growing the diameter of the given sphere until the coordinates of the given sphere intersect coordinates of the wall, wherein the processor is configured to find the set of one or more points for which the respective minimum distance is the local maximum relative to neighboring points in the plurality by finding a sphere set of one or more spheres for which the respective grown diameters are a local maximum relative to the respective grown diameters of neighboring grown spheres in the plurality, and wherein the processor is configured to identify one of the points by identifying one of the spheres in the sphere set for which the respective grown diameter is minimal among the one or more spheres in the sphere set.

19. The apparatus according to claim 18, wherein the neighboring grown spheres comprise nearest-neighboring grown spheres to the given sphere.

20. The apparatus according to claim 11, wherein the points comprise spheres having an initial diameter, wherein the processor is configured to find the local minimum distance for each given point by growing the diameter and moving each given sphere until it gets stuck in the cavity, and wherein the processor is configured to identify one of the points by identifying one of the spheres in the sphere set having the shortest grown diameter.

21. A computer software product, the product comprising a non-transitory computer-readable medium, in which program instructions are stored, which instructions, when read by a computer, cause the computer:

to receive three-dimensional (3D) image data with respect to a 3D region comprising body tissue in a living body;

to segment the 3D image data so as to identify a cavity within the body tissue and a wall surrounding the cavity;

for each point among a plurality of points in the cavity, to find a respective minimum distance from the point to the wall;

to find, among the plurality of the points, a set of one or more points for which the respective minimum distance is a local maximum relative to neighboring points in the plurality; and to identify as an entrance to the cavity one of the points in the set for which the respective minimum distance is minimal among the one or more points in the set.

* * * * *